(12) United States Patent
Beverly et al.

(10) Patent No.: US 10,786,151 B2
(45) Date of Patent: Sep. 29, 2020

(54) OPHTHALMIC INSTRUMENT HAVING MULTIPLE MEASUREMENT UNITS

(71) Applicant: REICHERT, INC., Depew, NY (US)

(72) Inventors: David L. Beverly, Alden, NY (US); Russell J. Bonaventura, Williamsville, NY (US)

(73) Assignee: Reichert, Inc., Depew, NY (US)

( * ) Notice: Subject to any disclaimer, the term of this patent is extended or adjusted under 35 U.S.C. 154(b) by 305 days.

(21) Appl. No.: 16/100,708

(22) Filed: Aug. 10, 2018

(65) Prior Publication Data

US 2020/0046221 A1 Feb. 13, 2020

(51) Int. Cl.
| | |
|---|---|
| *A61B 3/103* | (2006.01) |
| *A61B 3/107* | (2006.01) |
| *A61B 3/16* | (2006.01) |
| *A61B 3/00* | (2006.01) |

(52) U.S. Cl.
CPC ............ *A61B 3/103* (2013.01); *A61B 3/0016* (2013.01); *A61B 3/107* (2013.01); *A61B 3/165* (2013.01)

(58) Field of Classification Search
CPC ......... A61B 3/152; A61B 3/107; A61B 3/103; A61B 3/16; A61B 3/165; A61B 3/0016
See application file for complete search history.

(56) References Cited

U.S. PATENT DOCUMENTS

| | | | | |
|---|---|---|---|---|
| 3,787,112 A | * | 1/1974 | Lyons ................. | A61B 3/1176 351/223 |
| 5,325,135 A | * | 6/1994 | Nakamura ........... | A61B 3/1005 351/205 |
| 7,364,298 B2 | | 4/2008 | Hayashi et al. | |
| 7,399,081 B2 | | 7/2008 | Mimura et al. | |
| 7,588,336 B2 | | 9/2009 | Honda et al. | |
| 7,682,022 B2 | | 3/2010 | Honda | |
| 7,794,082 B2 | | 9/2010 | Bergner et al. | |
| 7,841,717 B2 | | 11/2010 | Ito et al. | |
| 7,992,998 B2 | | 8/2011 | Bergner et al. | |
| 9,220,407 B2 | | 12/2015 | Yam et al. | |
| 2003/0193648 A1 | | 10/2003 | O'Brien et al. | |

(Continued)

FOREIGN PATENT DOCUMENTS

WO 2017182341 A1 10/2017

*Primary Examiner* — Bumsuk Won
*Assistant Examiner* — Ephrem Z Mebrahtu
(74) *Attorney, Agent, or Firm* — Hodgson Russ LLP

(57) ABSTRACT

An ophthalmic instrument includes a carrier positionable relative to a test subject, and first and second measurement units mounted on the carrier by corresponding first and second parallelogram linkages. The first measurement unit, for example an autorefractor/keratometer, performs a first type of ophthalmic measurement, and is guided by the first parallelogram linkage to move relative to the carrier simultaneously in forward and downward directions from an idle position to a measurement position. The second measurement unit, for example a tonometer, performs a second type of ophthalmic measurement, and is guided by the second parallelogram linkage to move relative to the carrier simultaneously in forward and upward directions from an idle position to a measurement position. The first and second measurement units may each have a respective optical axis which aligns with a fixed measurement axis of the carrier when the measurement unit is in its measurement position.

15 Claims, 16 Drawing Sheets

(56) References Cited

U.S. PATENT DOCUMENTS

2008/0314181 A1 12/2008 Schena
2009/0128778 A1* 5/2009 Honda .................. A61B 3/107
351/245
2016/0310003 A1 10/2016 Inuzuka

* cited by examiner

US 10,786,151 B2

OPHTHALMIC INSTRUMENT HAVING MULTIPLE MEASUREMENT UNITS

FIELD OF THE INVENTION

The present invention relates to an ophthalmic instrument having more than one measurement unit, wherein a chosen one of the measurement units is selectively alignable with an eye of a test subject to perform a corresponding ophthalmic measurement.

BACKGROUND OF THE INVENTION

It is known to provide an ophthalmic instrument having a plurality of different measurement units for performing different types of ophthalmic measurements on the eyes of a test subject. See, for example, U.S. Pat. Nos. 7,364,298; 7,399,081; 7,588,336; and 7,841,717. A challenge in designing this type of ophthalmic instrument is keeping the instrument spatially compact while accommodating more than one measurement unit in the instrument housing. Another challenge is ensuring accurate, repeatable, efficient, and safe alignment of each measurement unit with an eye of a test subject for measurement purposes.

One known approach is to stack the measurement units vertically in fixed relation to each other within a carrier, and to mount the carrier on an XYZ motion platform for movement of the carrier in three dimensions relative to a base of the instrument. The measurement units have respective optical axes at different locations on the carrier which must be aligned with an eye to be tested. Consequently, the ophthalmic instrument tends to be tall, and the carrier must undergo a coarse adjustment in the vertical direction to changeover from one measurement unit to another.

A variation of the approach mentioned above is to provide reflective elements selectively insertable into the optical axis of a first measurement unit to fold the optical axis of a second measurement unit into the optical axis of the first measurement unit. This variation can economize alignment motion, but provision of additional optical elements adds cost and complexity to the instrument, and introduces further sources of measurement error into the optical path. Also, the overall height of the instrument is not reduced.

SUMMARY OF THE INVENTION

An ophthalmic instrument formed according to an embodiment of the present invention generally comprises a carrier positionable relative to a test subject, and first and second measurement units mounted to the carrier by corresponding first and second parallelogram linkages. The first measurement unit is operable to perform a first type of ophthalmic measurement, and is guided by the first parallelogram linkage to move relative to the carrier simultaneously in a forward direction and a downward direction from a first unit idle position to a first unit measurement position. The second measurement unit is operable to perform a second type of ophthalmic measurement, and is guided by the second parallelogram linkage to move relative to the carrier simultaneously in a forward direction and an upward direction from a second unit idle position to a second unit measurement position.

The ophthalmic instrument may have a measurement axis at a fixed location on the carrier, and each of the first and second measurement units may have a respective optical axis which is aligned with the measurement axis when the measurement unit is in its measurement position. The first unit measurement position and the second unit measurement position may be mutually exclusive, i.e. only one of the first and second measurement units can occupy its measurement position at any given time due to spatial overlap of the measurement positions.

The ophthalmic instrument may further comprise a first motor connected to the first parallelogram linkage for driving movement of the first measurement unit between the first unit idle position and the first unit measurement position, and a second motor connected to the second parallelogram linkage for driving movement of the second measurement unit between the second unit idle position and the second unit measurement position.

In an example embodiment of the invention, the first measurement unit includes a keratometer operable to measure corneal curvature and an autorefractor operable to measure refractive error, and the second measurement unit includes a non-contact tonometer operable to measure intraocular pressure. However, the nature of each measurement unit is subject to design choice.

The present invention provides a spatially compact ophthalmic instrument capable of performing different types of ophthalmic measurements utilizing a single measurement axis. Insertion of a chosen measurement unit into its measurement position, and retraction of another measurement unit to its idle position, is carried out in a smooth, quiet, and accurate manner by operation of the respective parallelogram linkages.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1:
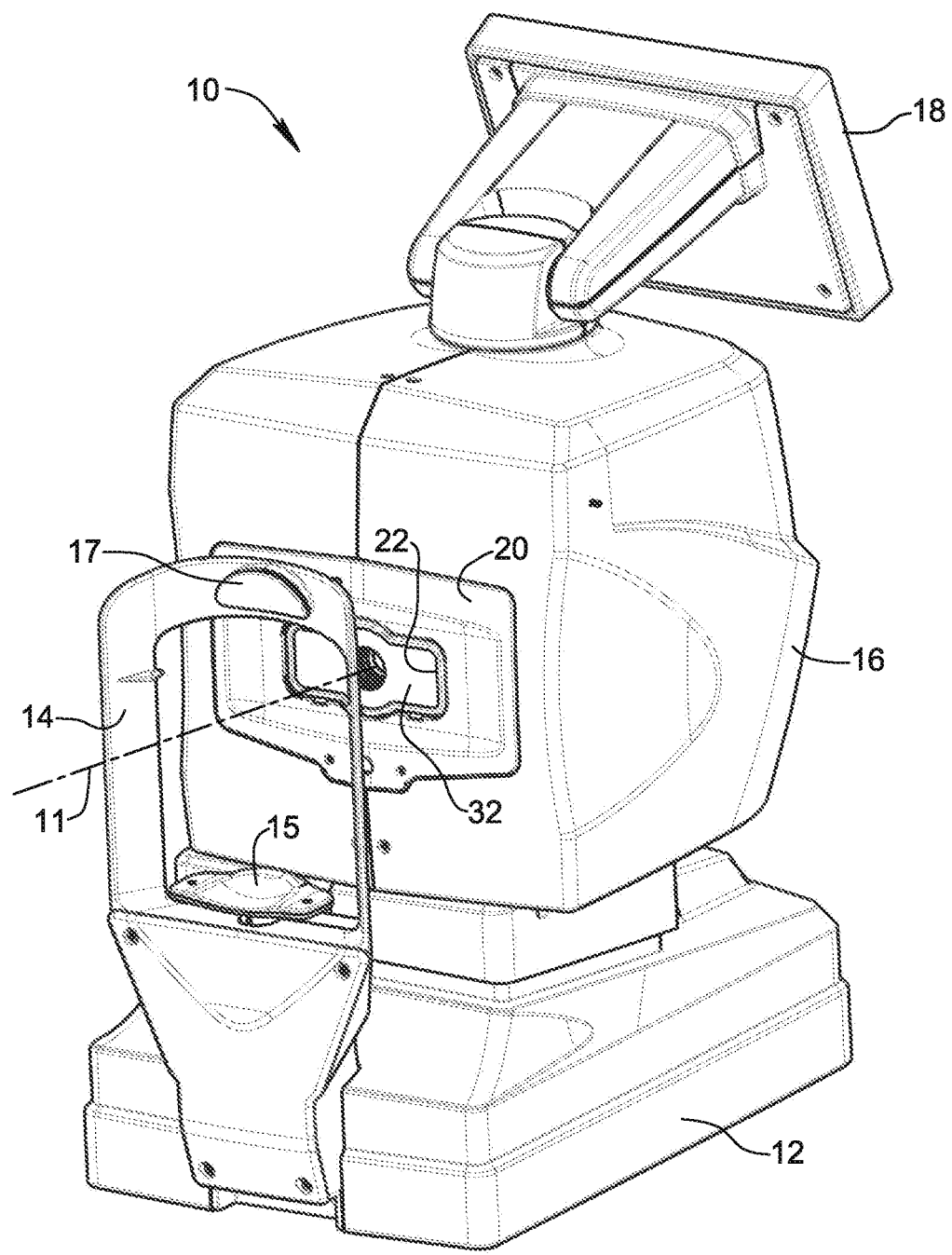
FIG. 1 is a perspective view showing an ophthalmic instrument formed in accordance with a first embodiment of the present invention.

FIG. 1 is a perspective view showing an ophthalmic instrument 10 formed in accordance with a first embodiment of the present invention. Ophthalmic instrument 10 generally comprises a stationary base 12, a test subject support 14 fixed to the base, a carrier 16 movable relative to base 12 and test subject support 14, and a user interface 18 mounted on carrier 16. Carrier 16 supports and houses a plurality of measurement units operable to perform various types of ophthalmic measurements on a test subject. As may be understood, test subject support 14 may include a chin rest 15 and a forehead rest 17 for positioning and stabilizing the head of a test subject to face carrier 16. Ophthalmic instrument 10 also has a measurement axis 11 at a fixed location relative to carrier 16 (i.e. the measurement axis 11 travels with carrier 16).

Carrier 16 may include a front cover 20 defining an opening 22 which receives a front panel of a chosen measurement unit. In FIG. 1, the front panel is identified by reference number 32 and is associated with a first measurement unit 30 that is visible in FIGS. 6-8 and 11. In the present embodiment, carrier 16 further supports and houses a second measurement unit 50 that is also visible in FIGS. 6-8 and 11. Second measurement unit 50 may include its own front panel 52.

Each of the measurement units 30, 50 is selectively alignable with an eye of a test subject to perform respective ophthalmic measurements. As may be understood from FIGS. 2-5, a selected measurement unit 30 or 50 is movable relative to carrier 16 so that the front panel 32 or 52 of the measurement unit is received by the opening 22 in the front cover 20 of carrier 16 and faces the test subject.

First measurement unit 30 may be, for example, an automatic keratometer/refractor operable to automatically measure corneal curvature and refractive error of a test subject's eye. Such a measurement unit may be found in the OPTOCHEK™ Plus Auto Refractor+Keratometer available from Reichert, Inc. of Depew, N.Y., U.S.A. First measurement unit 30 has a first optical axis 31 which must be aligned with a test subject's eye in order to perform a measurement. Thus, first optical axis 31 of first measurement unit 30 must be positioned to coincide with overall measurement axis 11 of ophthalmic instrument 10 when it is desired to use first measurement unit 30 to perform a measurement.

Second measurement unit 50 may be, for example, non-contact tonometer operable to measure intraocular pressure of a test subject's eye. Such a measurement unit may be found in the REICHERT® 7 Auto Tonometer and REICHERT® 7CR Auto Tonometer available from Reichert, Inc. of Depew, N.Y., U.S.A. Second measurement unit 50 has a second optical axis 51 which must be aligned with a test subject's eye in order to perform a measurement. When second measurement unit 50 is used to perform a measurement, second optical axis 51 associated with second measurement unit 50 must be positioned to coincide with measurement axis 11 of ophthalmic instrument 10.

Figure 2:
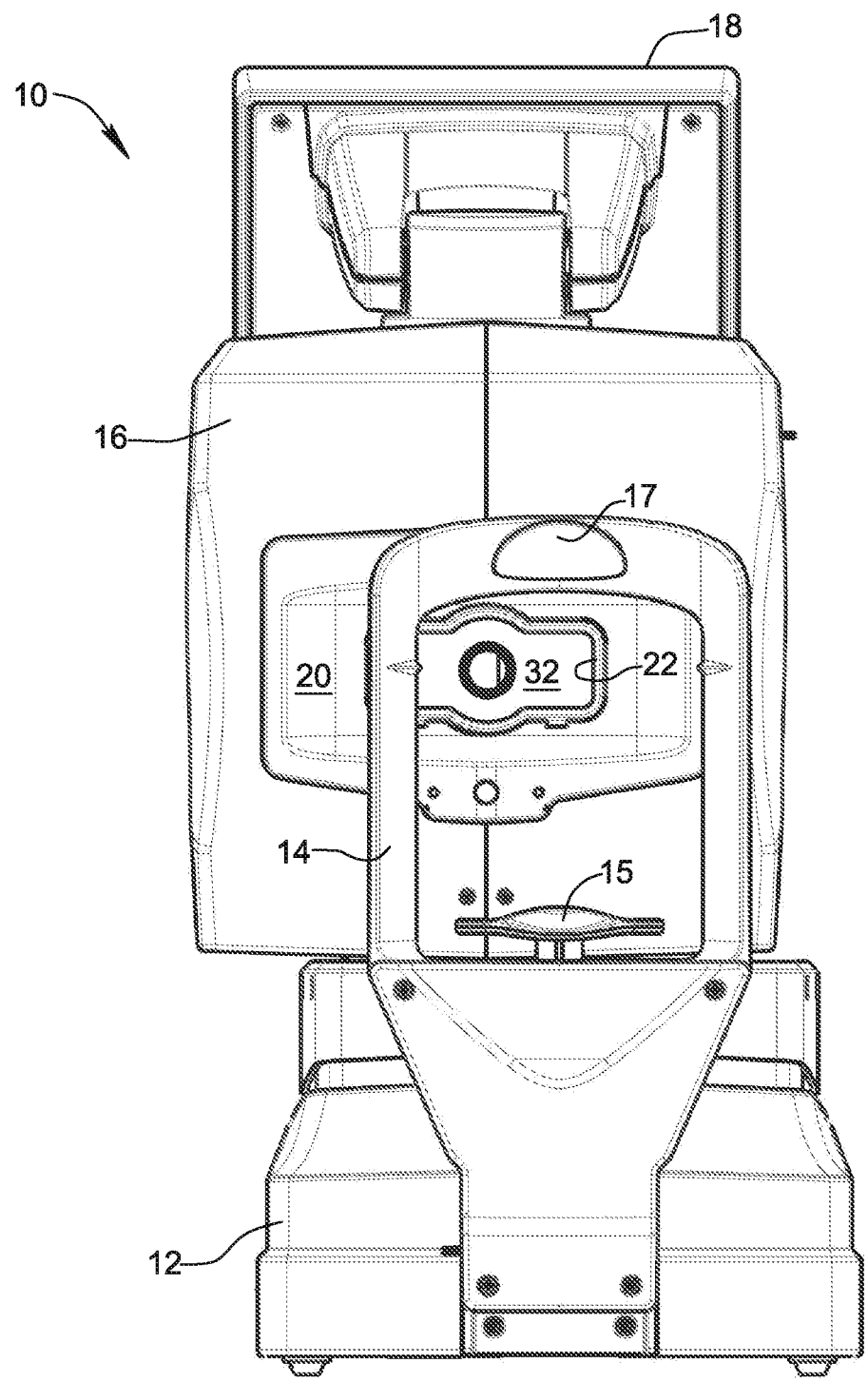
FIG. 2 is a front elevational view of the ophthalmic instrument shown in FIG. 1, wherein a first measurement unit of the ophthalmic instrument is aligned to measure the left eye of a test subject.
Figure 3:
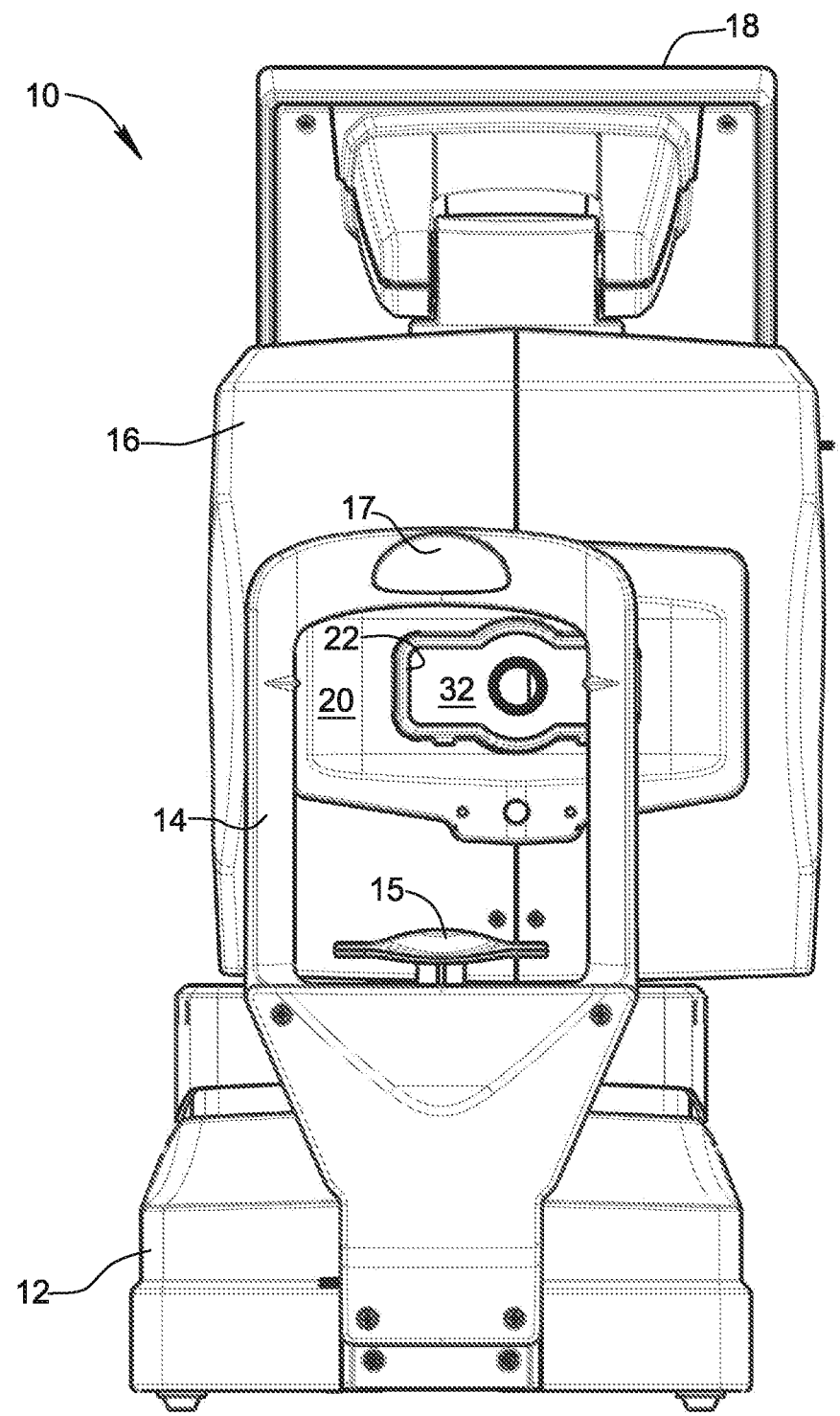
FIG. 3 is a front elevational view similar to that of FIG. 2, wherein the first measurement unit of the ophthalmic instrument is aligned to measure the right eye of a test subject.
Figure 4:
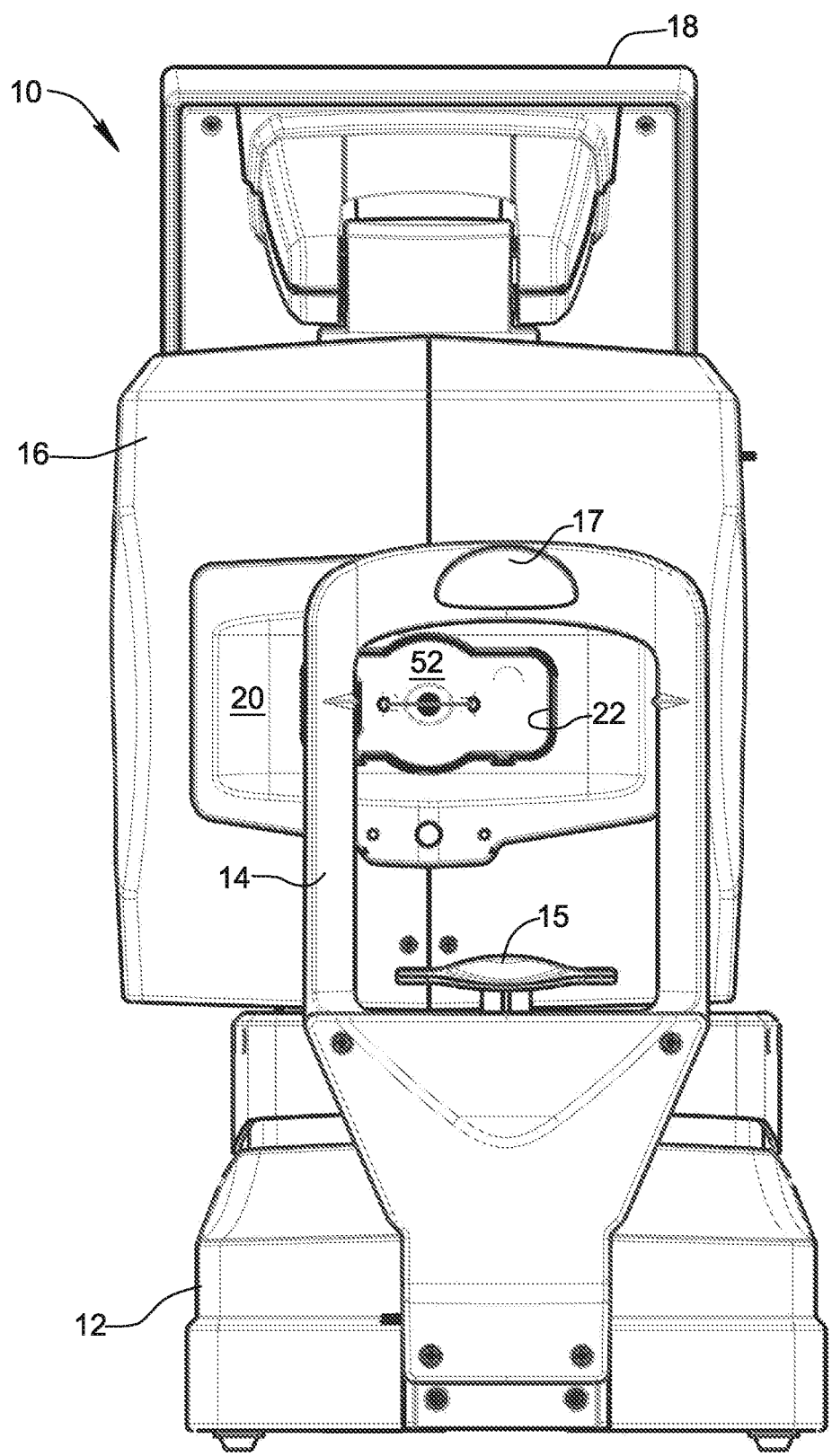
FIG. 4 is a front elevational view similar to that of FIG. 2, wherein a second measurement unit of the ophthalmic instrument is aligned to measure the left eye of a test subject.
Figure 5:
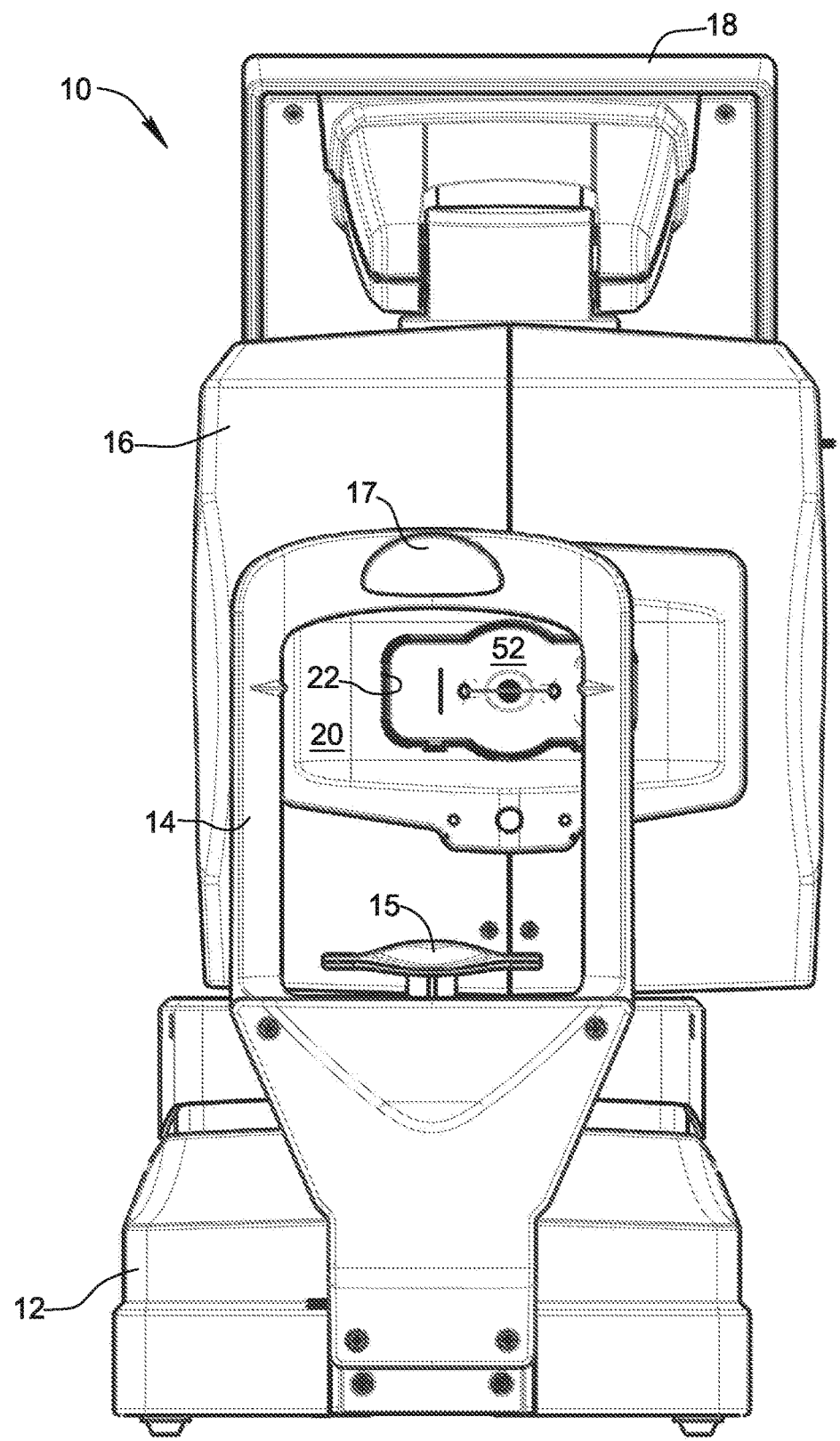
FIG. 5 is a front elevational view similar to that of FIG. 4, wherein the second measurement unit of the ophthalmic instrument is aligned to measure the right eye of a test subject.
Figure 14:
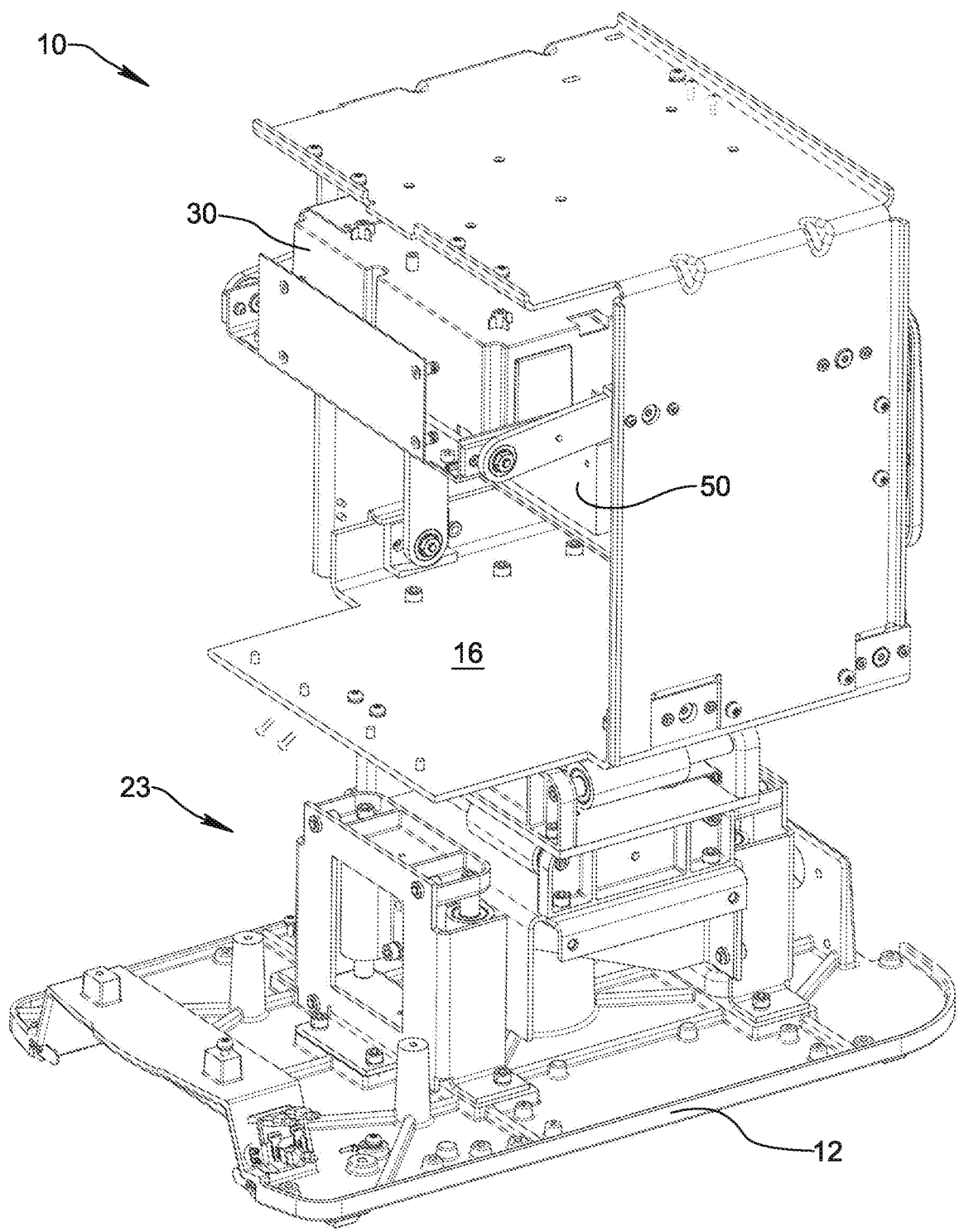
FIG. 14 is a generally rear perspective view of the ophthalmic instrument with its outer cover removed to reveal an XYZ motion platform thereof.

Carrier 16 is movable relative to base 12 and test subject support 14 along orthogonal X, Y, and Z axes so that the optical axis 31 or 51 of the chosen measurement unit 30 or 50 may be selectively aligned with each eye of a test subject. For example, FIG. 2 illustrates an alignment condition in which first measurement unit 30 is positioned to measure a left eye of a test subject, and FIG. 3 illustrates an alignment condition in which first measurement unit 30 is positioned to measure a right eye of a test subject. Similarly, FIG. 4 illustrates an alignment condition in which second measurement unit 50 is positioned to measure a left eye of a test subject, and FIG. 5 illustrates an alignment condition in which second measurement unit 50 is positioned to measure a right eye of a test subject. Carrier 16 may be mounted on base 12 by an XYZ motion platform 23 shown in FIGS. 14 and 15. XYZ motion platform 23 may include an X-axis drive motor 24, a Y-axis drive motor 25, and a Z-axis drive motor 26 controllable by an XYZ motor controller 28 to displace of carrier 16 relative to base 12 in the X, Y, and Z directions. XYZ motion platform 23 may further include an XYZ position detection circuit 29 providing positional information in three dimensions as feedback to XYZ motor controller 28.

In the present embodiment, first measurement unit 30 is located directly above second measurement unit 50, and ophthalmic instrument 10 includes a first parallelogram linkage 40 by which first measurement unit 30 is mounted to carrier 16 and a second parallelogram linkage 60 by which second measurement unit 50 is mounted to carrier 16.

Figure 6:
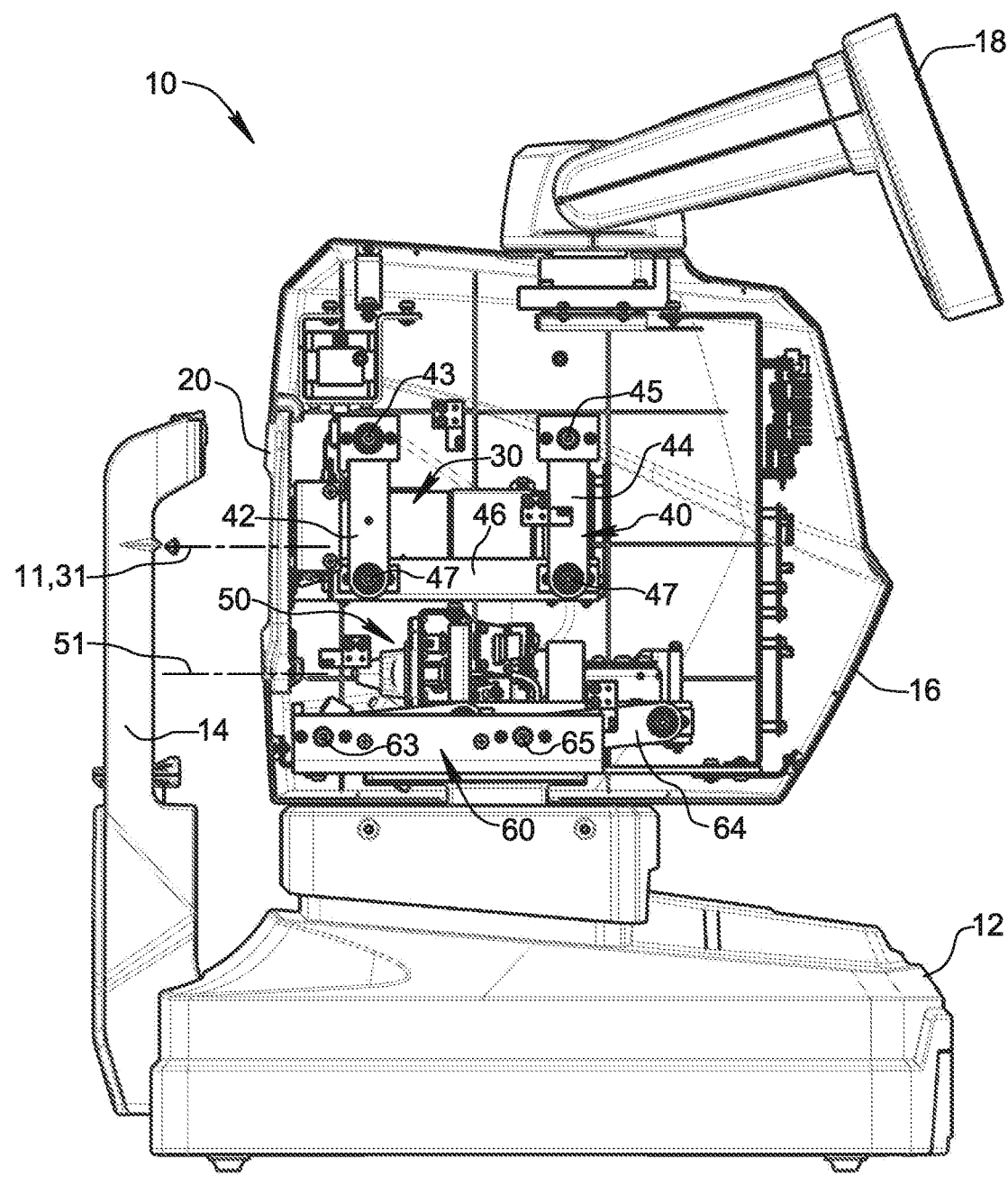
FIG. 6 is a side elevational view of the ophthalmic instrument shown in FIG. 1, partially sectioned to show mounting of the first and second measurement units in a movable carrier of the ophthalmic instrument, wherein the first measurement unit is shown in a first unit measurement position and the second measurement unit is shown in a second unit idle position.

As will be understood, first measurement unit 30 is movable relative to carrier 16 simultaneously in both a forward direction and a downward direction from a first unit idle position (FIG. 7) to a first unit measurement position (FIG. 6). First parallelogram linkage 40 constrains the motion of first measurement unit 30 relative to carrier 16 to an arcuate path while maintaining first optical axis 31 in a horizontal orientation. The dimensions of first measurement unit 30 and first parallelogram linkage 40 may be selected such that when first measurement unit 30 is shifted into the first unit measurement position under the guidance of first parallelogram linkage 40, first optical axis 31 will coincide with measurement axis 11 of ophthalmic instrument 10.

Figure 7:
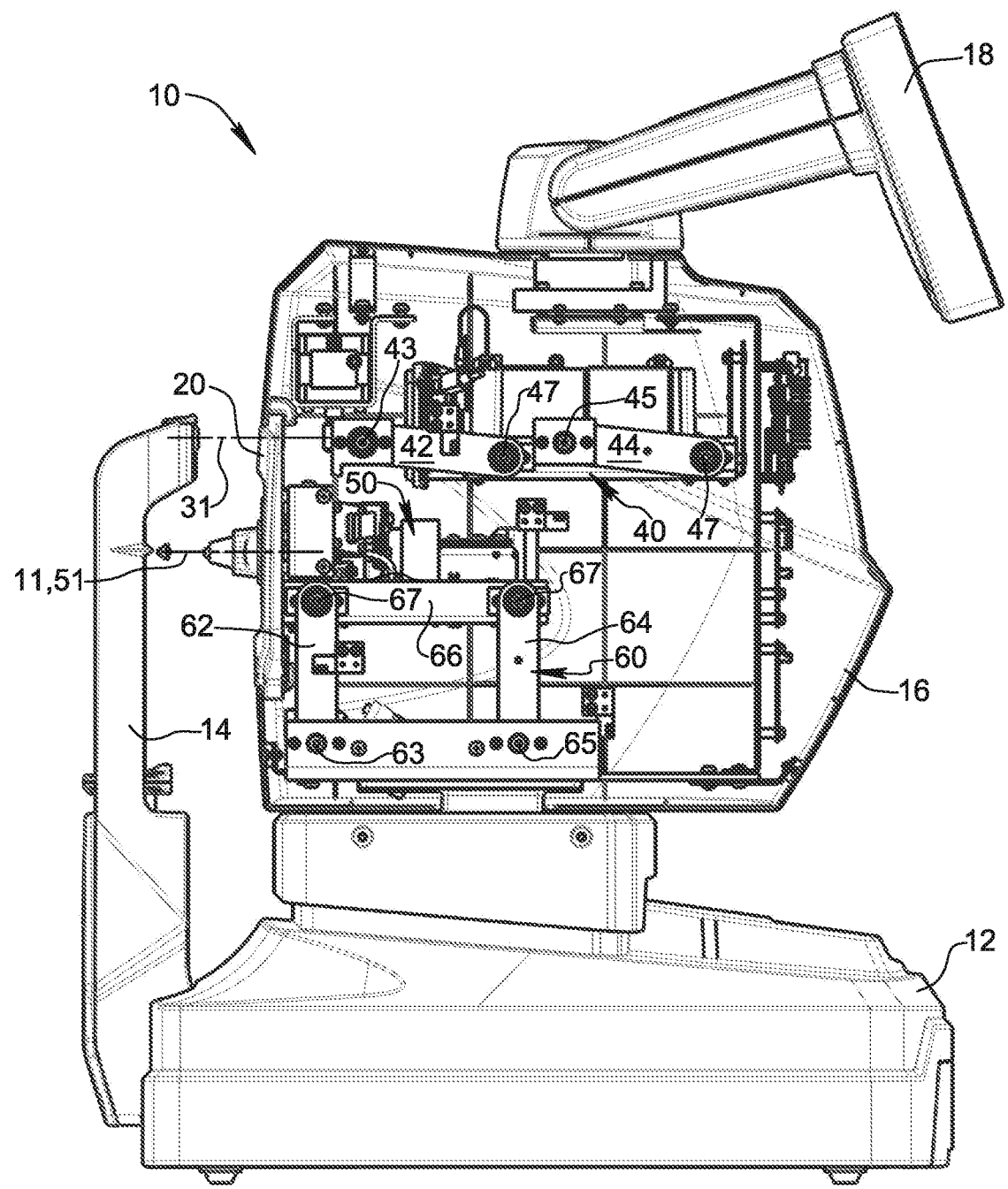
FIG. 7 is a side elevational view of the ophthalmic instrument similar to that of FIG. 6, wherein the first measurement unit is shown in a first unit idle position and the second measurement unit is shown in a second unit measurement position.

In similar fashion, second measurement unit 50 is movable relative to carrier 16 simultaneously in both a forward direction and an upward direction from a second unit idle position (FIG. 6) to a second unit measurement position (FIG. 7). Second parallelogram linkage 60 constrains the motion of second measurement unit 50 relative to carrier 16 to an arcuate path while maintaining second optical axis 51 in a horizontal orientation. The dimensions of second measurement unit 50 and second parallelogram linkage 60 may be chosen such that when second measurement unit 50 is moved into the second unit measurement position under the guidance of second parallelogram linkage 60, second optical axis 51 will coincide with measurement axis 11 of ophthalmic instrument 10.

As will be understood, the first unit measurement position and the second unit measurement position are mutually exclusive. In other words, first measurement unit 30 cannot occupy the first unit measurement position at the same time that second measurement unit 50 occupies the second unit measurement position. In the embodiment shown, first parallelogram linkage 40 and second parallelogram linkage 60 are arranged generally in a mirror image relation to one another, thereby helping to keep carrier 16 to a compact size. Because each optical axis 31, 51 is selectively brought into alignment with measurement axis 11 when the associated measurement is desired, it is unnecessary to displace carrier 16 vertically when switching over from one type of measurement to another type of measurement.

Figure 8:
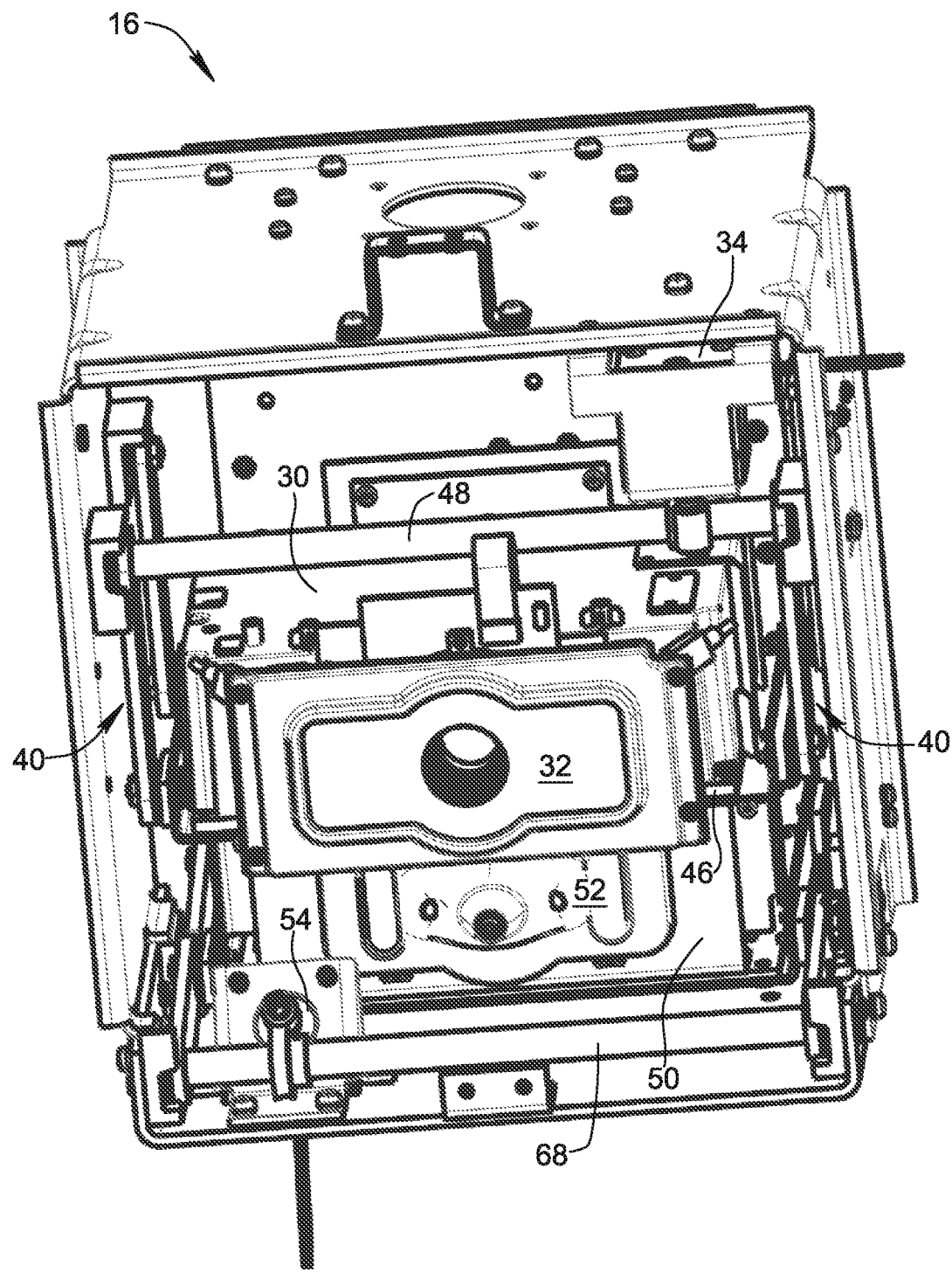
FIG. 8 is a generally frontal perspective view of the carrier and the first and second measurement units carried thereby, wherein the first measurement unit is shown in the first unit measurement position and the second measurement unit is shown in the second unit idle position.
Figure 9:
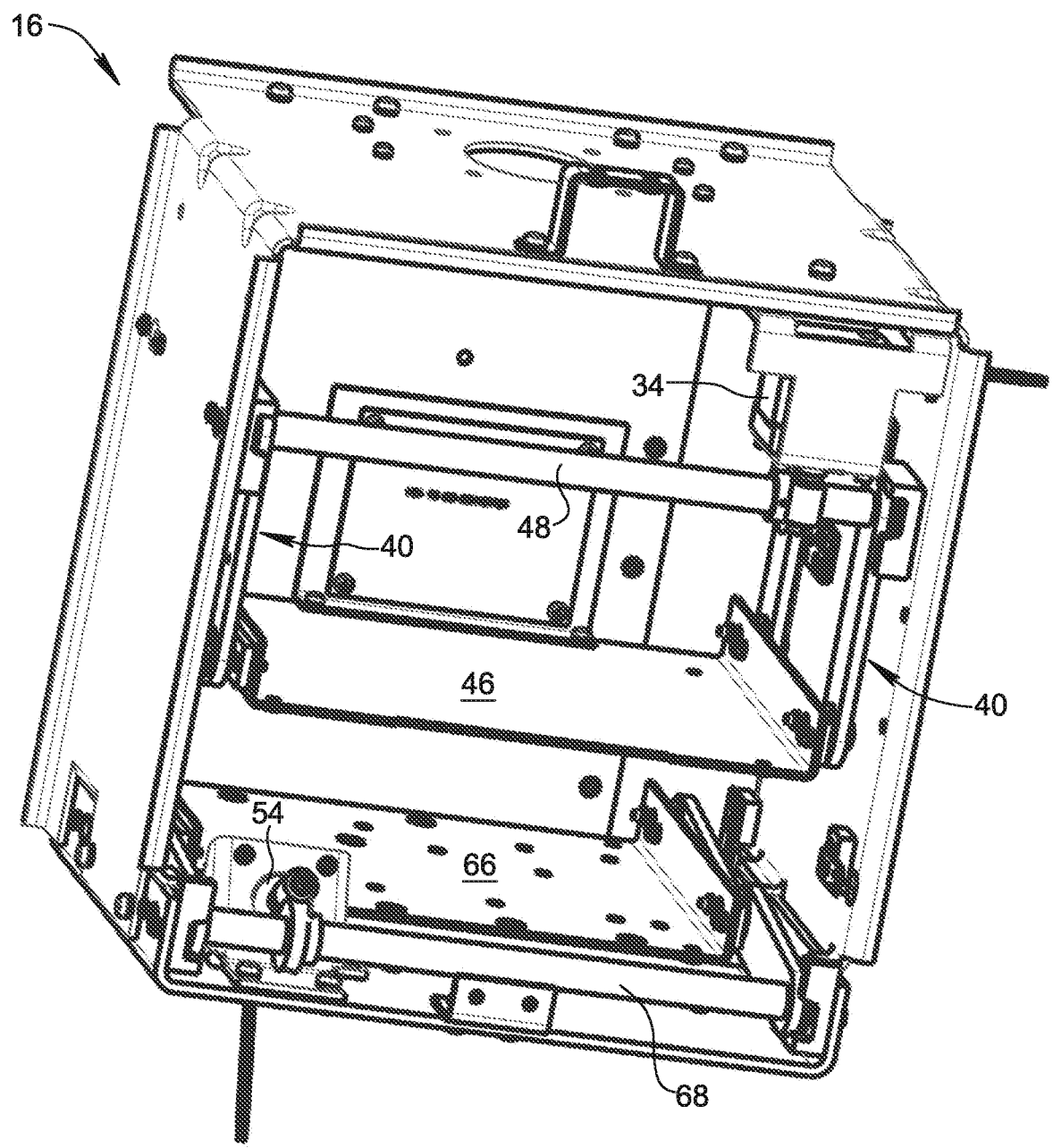
FIG. 9 is another generally frontal perspective view of the carrier shown in FIG. 8, wherein the first and second measurement units are removed to reveal mounting and drive structure for positioning the measurement units relative to the carrier.

As best seen in FIG. 6, first parallelogram linkage 40 includes a first link 42 having an upper end portion pivotally mounted to carrier 16 at a pivot 43, a second link 44 having an upper end portion pivotally mounted to carrier 16 at a pivot 45, and a third link 46 having opposite end portions pivotally coupled to respective lower end portions of the first and second links at a pair of pivots 47. As will be understood, a stationary fourth link of first parallelogram linkage 40 is formed by structure of carrier 16 between pivots 43 and 45. As shown in FIGS. 8 and 9, first parallelogram linkage 40 may be paired with a counterpart first parallelogram linkage 40 on an opposite lateral side of ophthalmic instrument 10, and third link 46 may be a laterally extending support plate shared by the paired linkages 40 and configured to support first measurement unit 30 from below.

Figure 12:
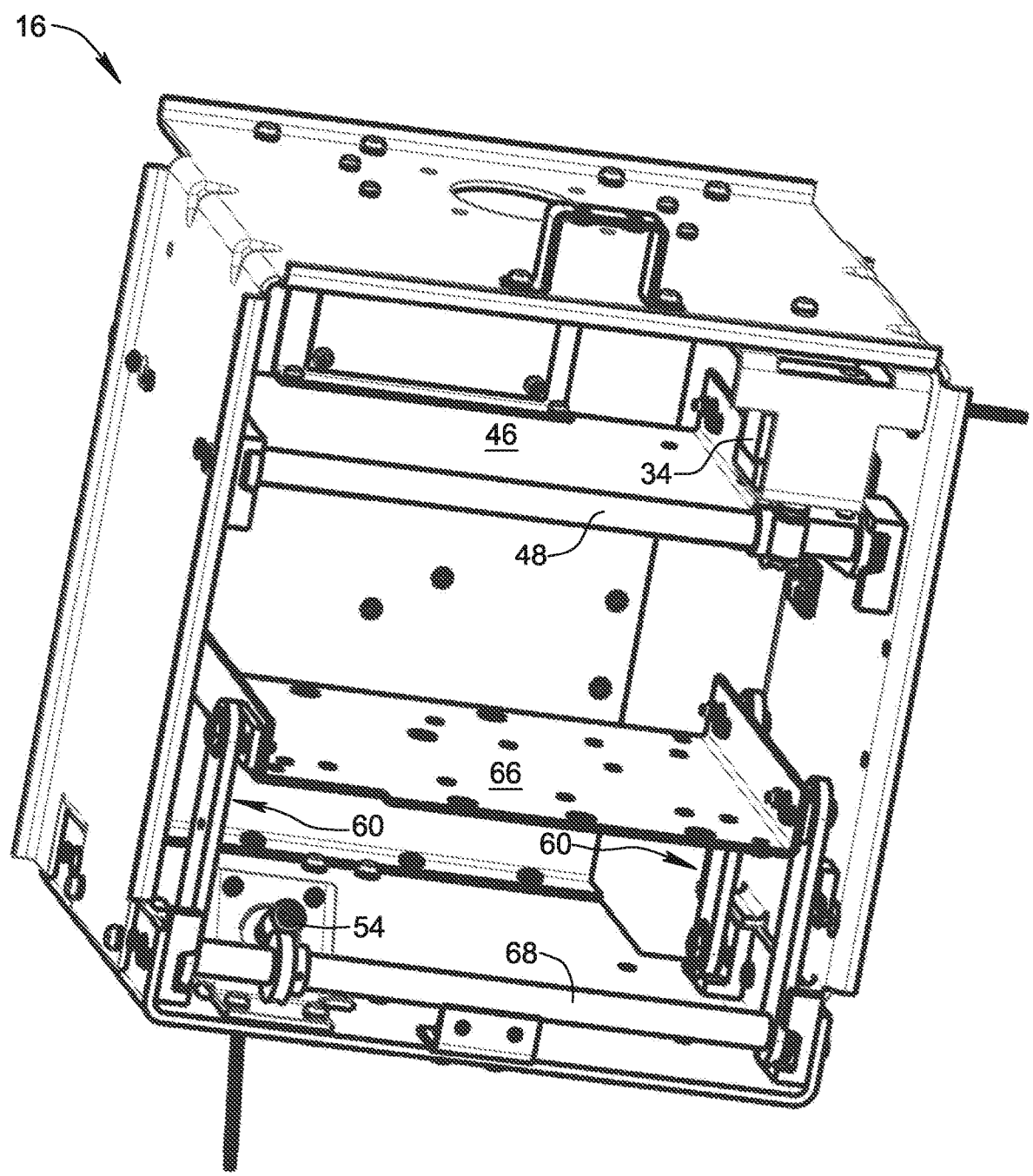
FIG. 12 is another generally frontal perspective view of the carrier shown in FIG. 11, wherein the first and second measurement units are removed.

As shown in FIG. 7, second parallelogram linkage 60 includes a first link 62 having a lower end portion pivotally mounted to carrier 16 at a pivot 63, a second link 64 having a lower end portion pivotally mounted to carrier 16 at a pivot 65, and a third link 66 having opposite end portions pivotally coupled to respective upper end portions of the first and second links at a pair of pivots 67. A stationary fourth link of second parallelogram linkage 60 is formed by structure of carrier 16 between pivots 63 and 65. As may be seen in FIGS. 11 and 12, second parallelogram linkage 60 may be paired with a counterpart second parallelogram linkage 60 on an opposite lateral side of ophthalmic instrument 10, and third link 66 may be a laterally extending support plate shared by the paired linkages 60 and configured to support second measurement unit 50 from below.

Ophthalmic instrument 10 may comprise motors for automatically driving movement of first measurement unit 30 between the first unit idle position and the first unit measurement position and movement of second measurement unit 50 between the second unit idle position and the second unit measurement position. For example, a first motor 34 may be connected to first parallelogram linkage 40 for driving movement of first measurement unit 30 between the first unit idle position and the first unit measurement position, and a second motor 54 connected to second parallelogram linkage 60 for driving movement of second measurement unit 50 between the second unit idle position and the second unit measurement position.

Figure 10:
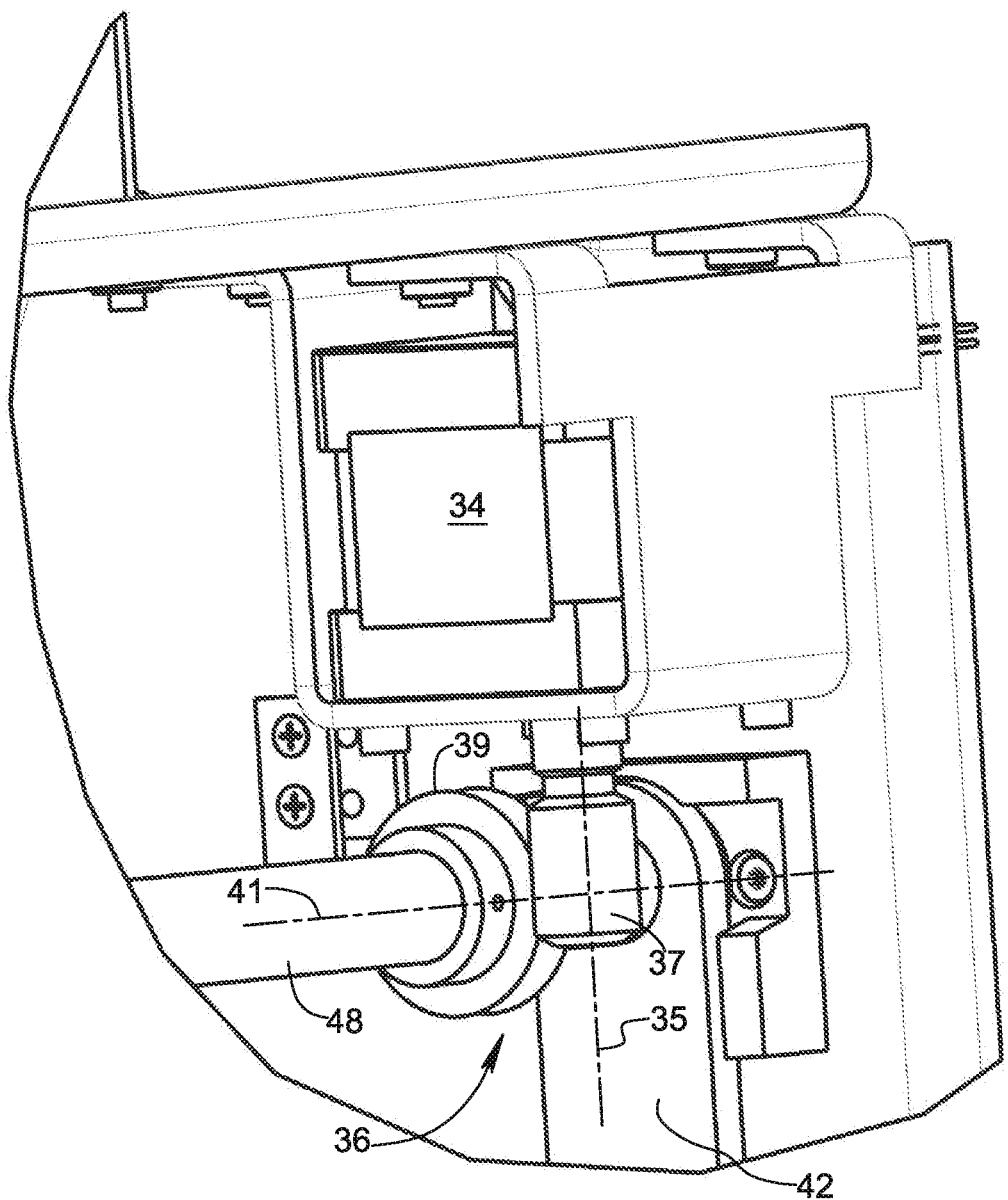
FIG. 10 is a close-up perspective view showing a first motor and a first drive assembly for automated positioning of the first measurement unit.
Figure 11:
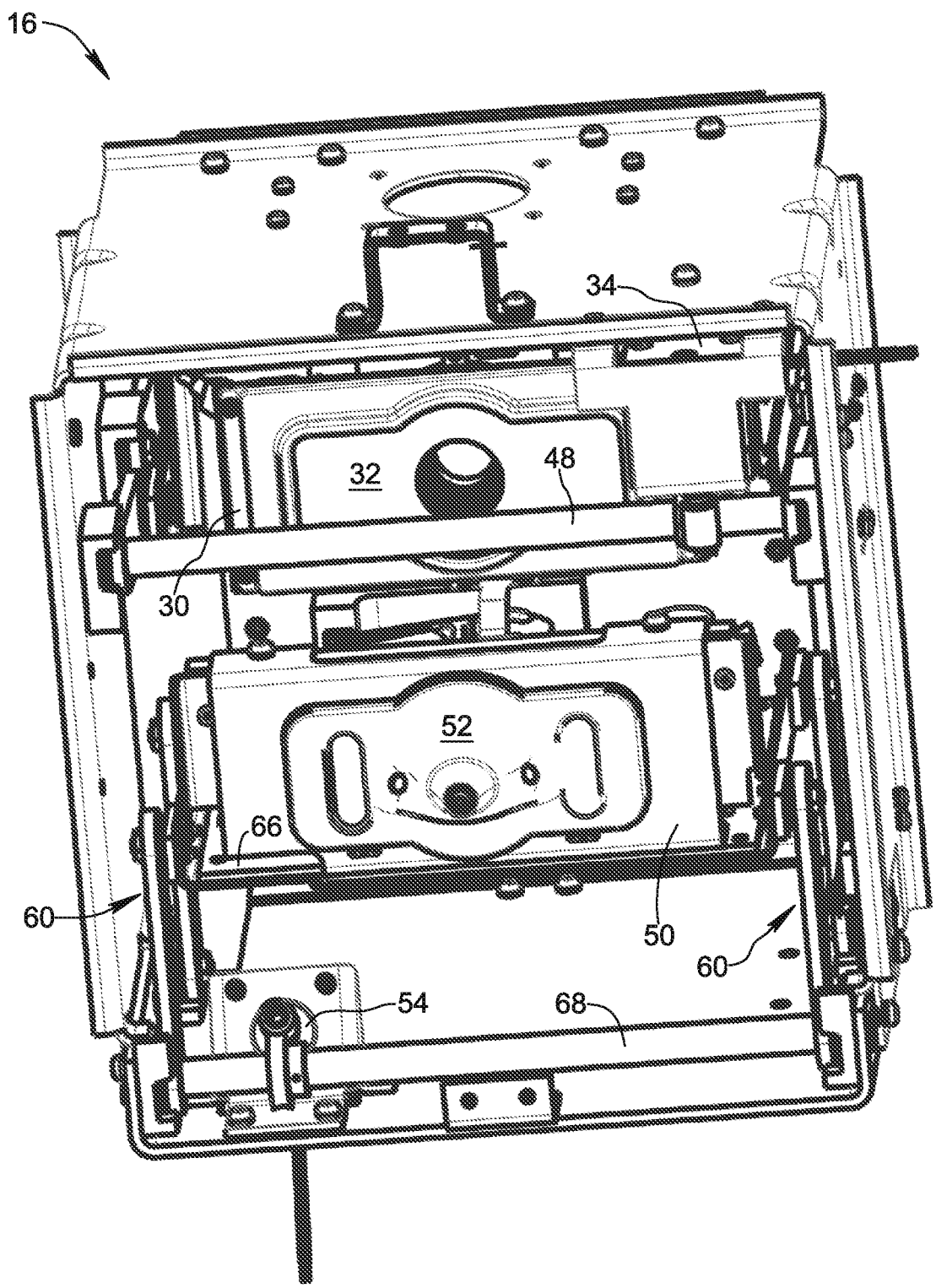
FIG. 11 is a generally frontal perspective view similar to that of FIG. 8, wherein the first measurement unit is shown in the first unit idle position and the second measurement unit is shown in the second unit measurement position.

As best seen in FIG. 10, first link 42 of first parallelogram linkage 40 may be a driven link, wherein first motor 34 is connected to first link 42 by a first drive assembly 36. In the embodiment shown, first drive assembly 36 is configured to pivot the driven link 42 of first parallelogram linkage 40 about an axis 41 extending orthogonal to a rotational axis 35 of first motor 34. First drive assembly 36 may include cylindrical worm 37 driven by first motor 34 and arranged in meshing engagement with a worm wheel 39 fixed to a laterally extending axle 48. Opposite end portions of axle 48 are coupled to respective first links 42 of paired first parallelogram linkages 40, only one lateral side being shown in FIG. 10. Thus, operation of first motor 34 will drive first links 42 to rotate about pivot 43.

Figure 13:
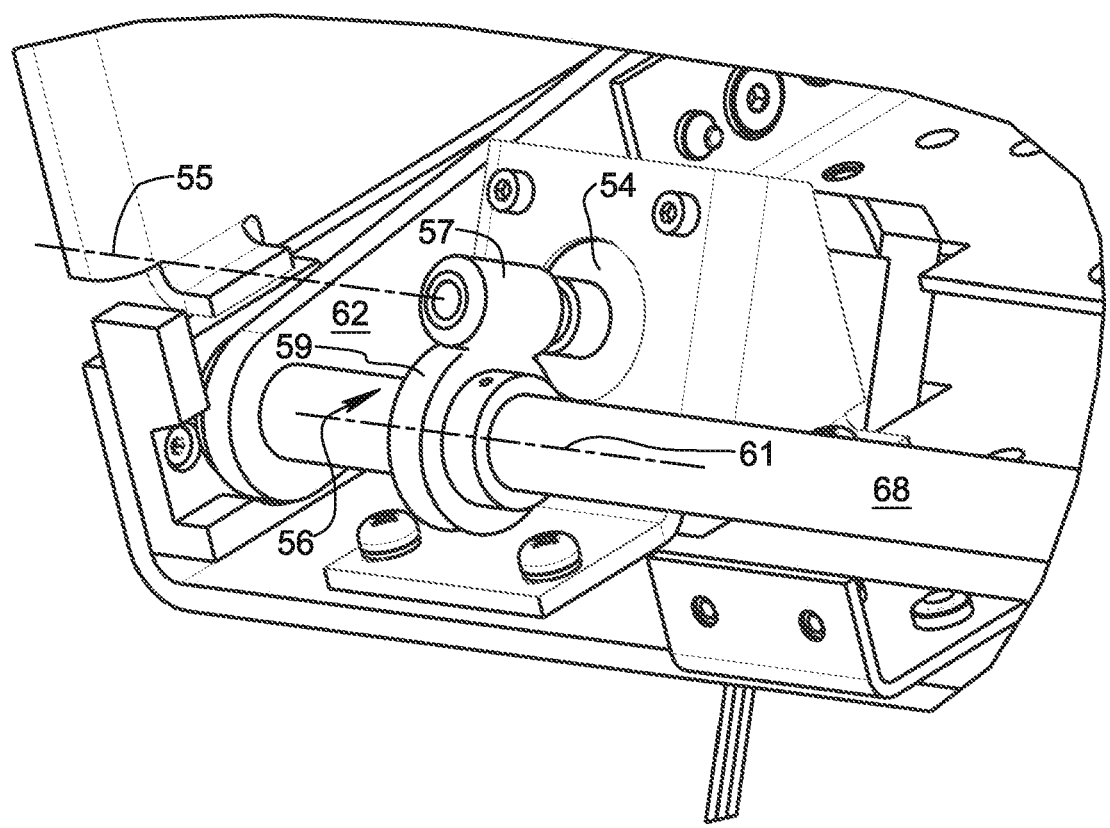
FIG. 13 is a close-up perspective view showing a second motor and a second drive assembly for automated positioning of the second measurement unit.

Similarly, as best seen in FIG. 13, first link 62 of second parallelogram linkage 60 may be a driven link, wherein second motor 54 is connected to first link 62 by a second drive assembly 56. Second drive assembly 56 may be configured to pivot the driven link 62 of second parallelogram linkage 60 about an axis 61 extending orthogonal to a rotational axis 55 of second motor 54. Second drive assembly 56 may include cylindrical worm 57 driven by second motor 54 and arranged in meshing engagement with a worm wheel 59 fixed to a laterally extending axle 68. Opposite end portions of axle 68 are coupled to respective first links 62 of paired second parallelogram linkages 60, only one lateral side being shown in FIG. 13. As may be understood, operation of second motor 54 will drive second links 62 to rotate about pivot 63.

Figure 15:
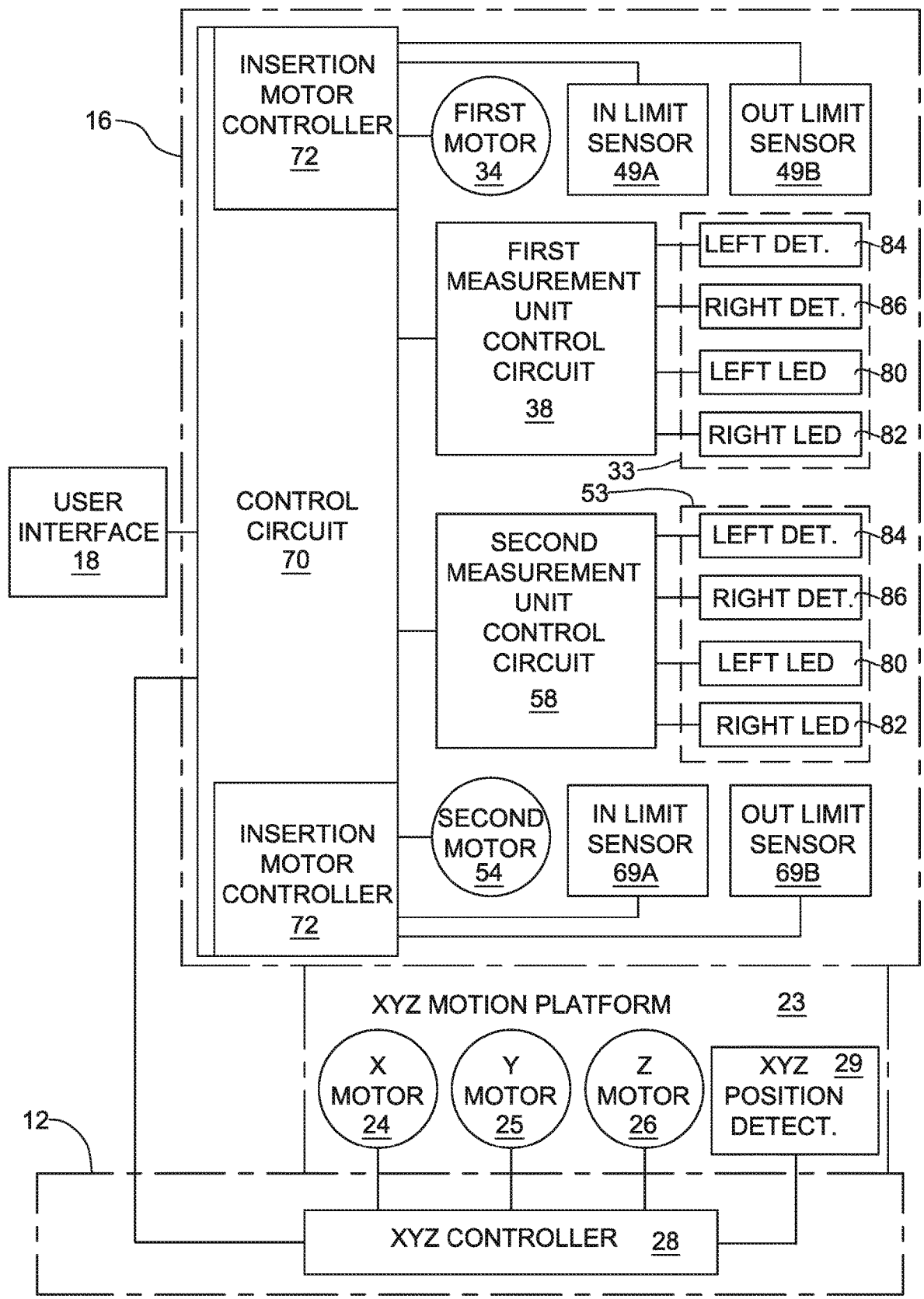
FIG. 15 is a block diagram schematically showing control electronics of the ophthalmic instrument.

Reference is made now to the schematic diagram of FIG. 15. User interface 18, which may be embodied as a menu-based touchscreen, keypad, voice-controlled interface, or any combination thereof, allows a user to select either first measurement unit 30 or second measurement unit 50 as the current measurement unit. User interface 18 may be connected to communicate with a control circuit 70 onboard carrier 16, wherein control circuit 70 includes insertion motor controllers 72 for controlling first motor 34 to move first measurement unit 30 between its measurement and idle positions, and for controlling second motor 54 to move second measurement unit 50 between its measurement and idle positions. Limit sensors 49A, 49B may be arranged to detect an inward (forward) travel limit and an outward (rearward) travel limit of first measurement unit 30 and provide signals to the associated insertion motor controller 72. Likewise, limit sensors 69A, 69B may be arranged to detect an inward (forward) travel limit and an outward (rearward) travel limit of second measurement unit 50 and provide signals to the associated insertion motor controller 72.

Each of the first and second measurement units 30, 50 includes a respective opto-electronic alignment system 33, 53 configured to detect a position of the corresponding optical axis 31, 51 relative to an eye of a test subject when the corresponding measurement unit 30, 50 is in its measurement position. As mentioned above, when one of the first and second measurement units 30, 50 is in its measurement position, its optical axis 31, 51 will coincide with measurement axis 11 of ophthalmic instrument 10. Therefore, opto-electronic alignment systems 33, 53 enable alignment of measurement axis 11 with an eye of a test subject. Alignment in all three spatial dimensions, i.e. X, Y, and Z, may be carried out automatically by communication between the applicable opto-electronic alignment system 33, 53 and XYZ motor controller 28 in base 12. Each opto-electronic alignment system 33, 53 may include a left LED 80 and a right LED 82 arranged to emit a pair of oblique positioning beams intersecting each other at a central point along the corresponding optical axis 31, 51 at a predetermined working distance along the Z axis from the corresponding measurement unit 30, 50, and a left light-sensitive detector 84 and a right light-sensitive detector 86 arranged to receive the positioning beams after the positioning beams are reflected by the cornea of a test subject when the apex of the cornea is aligned on measurement axis 11 at the beam intersection point. Signals from light-sensitive detectors 84, 86 inform XYZ motor controller 28 of a current state of alignment and enable XYZ motor controller 28 to issue motion commands to X-axis drive motor 24, Y-axis drive motor 25, and Z-axis drive motor 26 to automatically achieve proper alignment. The light-sensitive detectors 84, 86 will register a peak signal when the eye of the test subject is properly aligned in the X, Y, and Z dimensions for a measurement, thereby confirming desired alignment just prior to measurement. When alignment is confirmed, a measurement may be triggered automatically or manually by an operator receiving confirmation of alignment on user interface 18.

Figure 16:
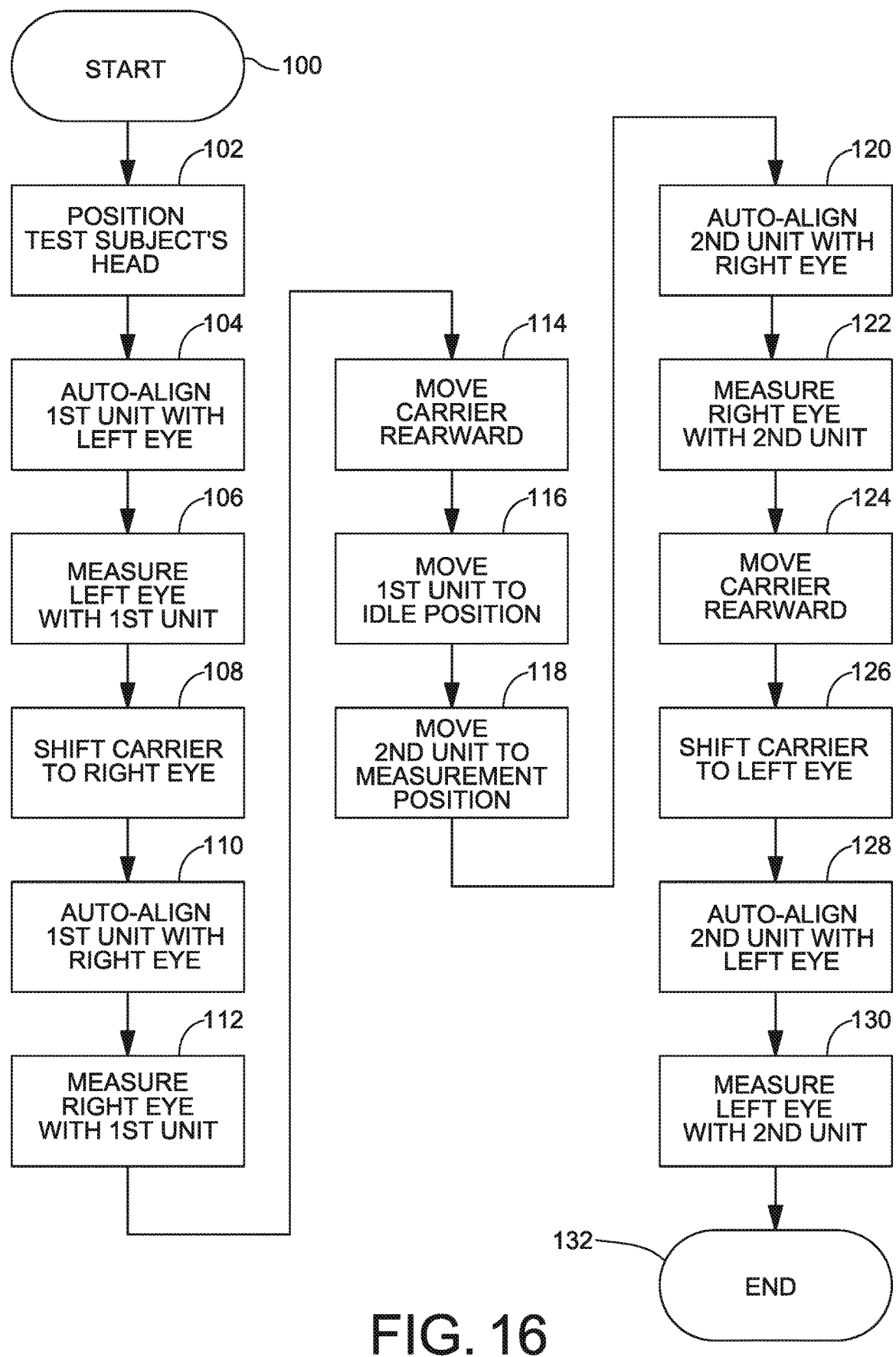
FIG. 16 is a flow diagram illustrating operation of ophthalmic instrument to perform ophthalmic measurements.

The sequence of a typical measurement process conducted using ophthalmic instrument 10 is now described with reference to FIG. 16. At start block 100, it is assumed that first measurement unit 30 is in its measurement position and second measurement unit 50 is in its idle position. In step 102, the test subject's head is positioned in test subject support 14. For example, test subject support 14 may have canthus markings to which the test subject's canthus is aligned when the patient's forehead is placed against forehead rest 17, and chin rest 15 may be adjusted in a vertical direction to meet and support the test subject's chin to stabilize the test subject's head.

In step 104, first measurement unit 30 is automatically aligned with the left eye of the test subject by operation of opto-electronic alignment system 33 in cooperation with XYZ motion platform 23. When first measurement unit 30 is properly aligned, measurement axis 11 and optical axis 31 coincide with one another and intersect the corneal apex, and first measurement unit 30 is located at a predetermined working distance from the eye along the Z-axis. By way of example, where first measurement unit 30 is embodied as an automatic keratometer/refractor, the predetermined working distance may be approximately 50 mm. Once alignment is achieved, at least one ophthalmic measurement of the test subject's left eye is made by first measurement unit 30 in step 106. After step 106 is completed, carrier 16 is shifted laterally in step 108 to be positioned generally in front of the test subject's right eye. Steps 110 and 112 are similar to steps 104 and 106, except automatic alignment and ophthalmic measurement are conducted with respect to the right eye of the test subject instead of the left eye. After both eyes have been measured by first measurement unit 30, carrier 16 may be moved rearward, i.e. away from the test subject, in step 114.

Ophthalmic measurements may then be carried out using second measurement unit 50. In step 116, first measurement unit 30 is moved from its measurement position to its idle position by operation of first motor 34. Second measurement unit 50 may then be moved from its idle position to its measurement position by operation of second motor 54 in accordance with step 118.

In step 120, second measurement unit 50 is automatically aligned with the right eye of the test subject by operation of opto-electronic alignment system 53 in cooperation with XYZ motion platform 23. When second measurement unit 50 is properly aligned, measurement axis 11 and optical axis 51 coincide with one another and intersect the corneal apex, and second measurement unit 50 is located at a predetermined working distance from the eye along the Z-axis. By way of example, where second measurement unit 50 is embodied as a non-contact tonometer, the predetermined working distance may be approximately 8.4 mm. Once alignment is achieved, at least one ophthalmic measurement of the test subject's right eye is made by second measurement unit 50 in step 122. After step 122 is completed, carrier 16 may be moved rearward away from the test subject in step 124, and then shifted laterally in step 126 to be positioned generally in front of the test subject's left eye. Steps 128 and 130 are similar to steps 120 and 122, except automatic alignment and ophthalmic measurement are conducted with respect to the left eye of the test subject instead of the right eye. The measurement process ends at block 132.

As may be understood, rearward displacement of carrier 16 at steps 114 and 124 is provided if the predetermined working distance of second measurement unit 50 is relatively close to the test subject's face so that the test subject is not made to feel anxious and there is no unintended contact with the test subject's face during movement of carrier 16.

It is noted that the above process description is based on initially measuring the left eye with first measurement unit 30. However, the process may be conducted starting with the test subject's right eye instead of the left eye, and it may be conducted starting with second measurement unit 50 instead of first measurement unit 30.

In an embodiment of the invention, step 102 is performed and then the operator may be prompted to press a start button or icon on user interface 18 to begin a fully automated sequence of steps 104 through 130, whereby both the left and right eyes are measured by first measurement unit 30 and by second measurement unit 50 in an efficient manner without the need for operator action or intervention.

In the example embodiment described herein, first measurement unit 30 includes a keratometer and an autorefractor, and the second measurement unit 50 includes a non-contact tonometer. However, the functional measurement units may be swapped, i.e. first measurement unit 30 may include a tonometer and second measurement unit 50 may include a keratometer and an autorefractor. The invention is not confined to keratometer, autorefractor, and/or tonometer measurement units; other types of measurement units may be provided for making other types of ophthalmic measurements without straying from the invention.

While the invention has been described in connection with exemplary embodiments, the detailed description is not intended to limit the scope of the invention to the particular forms set forth. The invention is intended to cover such alternatives, modifications and equivalents of the described embodiment as may be included within the scope of the claims.

What is claimed is:
1. An ophthalmic instrument comprising:
a carrier positionable relative to a test subject;
a first measurement unit operable to perform a first type of ophthalmic measurement;
a second measurement unit operable to perform a second type of ophthalmic measurement different from the first type of ophthalmic measurement;
a first parallelogram linkage by which the first measurement unit is mounted to the carrier, whereby the first measurement unit is guided to move relative to the carrier simultaneously in a forward direction and a downward direction from a first unit idle position to a first unit measurement position; and a second parallelogram linkage by which the second measurement unit is mounted to the carrier, whereby the second measurement unit is guided to move relative to the carrier simultaneously in both a forward direction and an upward direction from a second unit idle position to a second unit measurement position.

2. The ophthalmic instrument according to claim 1, wherein the ophthalmic instrument has a measurement axis at a fixed location relative to the carrier, the first measurement unit has a first optical axis aligned with the measurement axis when the first measurement unit is in the first unit measurement position, and the second measurement unit has a second optical axis aligned with the measurement axis when the second measurement unit is in the second unit measurement position.

3. The ophthalmic instrument according to claim 1, wherein the first unit measurement position and the second unit measurement position are mutually exclusive.

4. The ophthalmic instrument according to claim 1, further comprising:

a first motor connected to the first parallelogram linkage for driving movement of the first measurement unit between the first unit idle position and the first unit measurement position; and a second motor connected to the second parallelogram linkage for driving movement of the second measurement unit between the second unit idle position and the second unit measurement position.

5. The ophthalmic instrument according to claim 4, wherein the first parallelogram linkage includes a driven link, and the first motor is connected to the driven link of the first parallelogram linkage by a first drive assembly, and wherein the second parallelogram linkage includes a driven link, and the second motor is connected to the driven link of the second parallelogram linkage by a second drive assembly.

6. The ophthalmic instrument according to claim 5, wherein the first drive assembly is configured to pivot the driven link of the first parallelogram linkage about an axis extending orthogonal to a rotational axis of the first motor.

7. The ophthalmic instrument according to claim 5, wherein the second drive assembly is configured to pivot the driven link of the second parallelogram linkage about an axis extending orthogonal to a rotational axis of the second motor.

8. The ophthalmic instrument according to claim 1, further comprising:

a base; and a test subject support fixed to the base;

wherein the carrier is mounted on the base for movement relative to the test subject support.

9. The ophthalmic instrument according to claim 1, wherein the first measurement unit includes a keratometer operable to measure corneal curvature.

10. The ophthalmic instrument according to claim 1, wherein the first measurement unit includes an autorefractor operable to measure refractive error.

11. The ophthalmic instrument according to claim 9, wherein the first measurement unit further includes an autorefractor operable to measure refractive error.

12. The ophthalmic instrument according to claim 1, wherein the second measurement unit includes a non-contact tonometer operable to measure intra-ocular pressure.

13. The ophthalmic instrument according to claim 9, wherein the second measurement unit includes a non-contact tonometer operable to measure intra-ocular pressure.

14. The ophthalmic instrument according to claim 10, wherein the second measurement unit includes a non-contact tonometer operable to measure intra-ocular pressure.

15. The ophthalmic instrument according to claim 11, wherein the second measurement unit includes a non-contact tonometer operable to measure intra-ocular pressure.

* * * * *